United States Patent [19]

Hums

[11] Patent Number: 4,954,476
[45] Date of Patent: Sep. 4, 1990

[54] METHOD OF MAKING CATALYSTS FROM TITANIUM OXIDE

[75] Inventor: Erich Hums, Erlangen, Fed. Rep. of Germany

[73] Assignee: Siemens Aktiengesellschaft, Berlin and Munich, Fed. Rep. of Germany

[21] Appl. No.: 147,899

[22] Filed: Jan. 25, 1988

[30] Foreign Application Priority Data

Jan. 23, 1987 [DE] Fed. Rep. of Germany ....... 3701984

[51] Int. Cl.$^5$ ............................................. B01J 21/06
[52] U.S. Cl. ..................................... 502/350; 423/610
[58] Field of Search ................ 502/350, 242; 423/610, 423/239, 239 A

[56] References Cited

U.S. PATENT DOCUMENTS 4,113,660 9/1978 Abe et al. .............................. 502/208
4,207,209 6/1980 Matsuda et al. ................. 423/239 A
4,378,338 3/1983 Imanari et al. ................... 423/239 A
4,725,572 2/1988 Sera et al. ............................ 502/350

FOREIGN PATENT DOCUMENTS 0264747  4/1988  European Pat. Off. ............ 502/350
3634335  4/1988  Fed. Rep. of Germany ...... 502/350
3701984  8/1988  Fed. Rep. of Germany ...... 502/350
0039296  4/1978  Japan ..................................... 423/610
0210849 12/1983  Japan ..................................... 502/350
1085935  4/1984  U.S.S.R. ............................... 423/610

Primary Examiner—Robert L. Stoll
Attorney, Agent, or Firm—Herbert L. Lerner; Laurence A. Greenberg

[57] ABSTRACT

The method produces a catalyst containing titanium oxide as a primary ingredient and is prepared from a titanium oxide-containing starting material through a titanium oxide precursor containing a suitable meta or ortho-titanic acid. Meta or ortho-titanic acid is obtained through a hydrothermal process step carried out in the presence of a suitable flocculent or colloid.

17 Claims, No Drawings

METHOD OF MAKING CATALYSTS FROM TITANIUM OXIDE

The invention relates to a method for making a catalyst, which contains titanium oxide as the primary component thereof and which is made from a titania source starting material through a suitable titanium oxide precursor containing meta- or ortho-titanic acid.

German Patent DE-PS No. 26 58 569, corresponding to U.S. Pat. No. 4,113,660, discloses a method for making a shaped catalyst containing titanium oxide as the primary component thereof. This method uses a meta-titanic acid sol, which is prepared by the removal by flocculation of meta-titanic acid by the sulfuric acid process, the meta-titanic acid having been set at a pH value of 1 and higher. A particular feature of this prior art method of preparation of the primary component of the catalystic, titanium oxide, is that the titanium oxide is prepared through a titanium oxide sol.

It is accordingly an object of the invention to provide a method of making catalysts from titanium oxide, which overcomes the disadvantages of the heretofore-known methods of this general type and which avoids the intermediate stage of the titanium oxide sol.

With the foregoing and other objects in view there is provided, in accordance with the invention, in a method for making a catalyst containing titanium oxide as a primary ingredient and being prepared from a titania-source starting material through a titanium oxide precursor containing a suitable meta or ortho-titanic acid, the improvement which comprises obtaining meta or ortho-titanic acid through a hydrothermal process step carried out in the presence of a suitable flocculent or colloid.

If the precipitation through a titanium oxide sol corresponding to the prior art is replaced with a hydrothermal process step, in other words with agglomeration under pressure and temperature, then a different crystalline structure of the titanium oxide is obtained, which is better suited for use as a catalyst.

In accordance with another mode of the invention, there is provided a method which comprises using as flocculents suitable soluble compounds selected from the group consisting of soluble vanadium compounds, preferably ammonium vanadate, soluble phosphates, preferably phosphoric acid, soluble silicic acid compounds, soluble molybdenum compounds, preferably ammonium molybdate, soluble tungsten compounds, preferably ammonium tungstate, sulfuric acid or carbon, the latter possibly in the form of graphite powder.

The preparation of a catalyst by the method according to the invention can be carried out, for example, in such a way that meta or orthotitanic acid is agglomerated with one or more of the aforementioned flocculent additive substances, for instance soluble vanadium compounds, in the so-called hydrothermal process step. In other words, this hydrothermal step is done in an autoclave at an increased temperature and an increased pressure as compared with standard conditions, for example at 200° C. and 15 bar. After removal of the solvent, namely water, by decanting, from the precipitate the product which is obtained is dried. After decanting the water, a further operation can be added, in which the product that is obtained is rinsed one more time with water prior to drying, in order to free it of corresponding ionic excesses and or impurities. The composition which is present after the drying process can be mixed as needed with binders, such as phosphates. Next, after suitable shaping into granulates, extrusion into shaped bodies, or the coating of plates, expanded metals, meshes or the like, it can be calcined at temperatures of approximately 500° C. and thereby hardened.

In accordance with a further mode of the invention, there is provided a method which comprises subsequently calcining the agglomerated and precipitated product after or before a interposed shaping step.

The catalysts thus obtained can be used as reduction catalysts for reducing nitrogen oxides in the presence of ammonia.

Therefore, in accordance with an added mode of the invention, there is provided a method which comprises using the resultant product as a reduction catalyst for reducing nitrogen oxides in the presence of reducing agents from the group consisting of $NH_3$, CO and hydrocarbons.

In accordance with an additional mode of the invention, there is provided a method which comprises preparing phthalic acid anhydride from orthoxylol or maleic acid anhydride from $C_4$ hydrocarbons by using the catalyst product as an oxidation catalyst.

In accordance with a concomitant mode of the invention, there is provided a method which comprises shifting the method for titanium oxide preparation in the direction of increased rutile formation by means of suitable additions of rutilizing formers. In cases in which the catalyst material is to be present in a rutilized form (rutile is a particular crystal configuration of titanium oxide), then rutilizing formers, such as lithium or calcium salts or copper oxide of the meta and ortho-titanic acid, should be added before beginning the hydrothermal aforementioned process step with the titania source starting substance.

Other modes which are considered as characteristic for the invention are set forth in the appended claims.

Although the invention is described herein as embodied in a method of making catalysts from titanium oxide, it is nevertheless not intended to be limited to the details given, since various modifications may be made therein without departing from the spirit of the invention and within the scope and range of equivalents of the claims.

The method of operation of the invention, however, together with additional objects and advantages thereof will be best understood from the following description of a specific example.

EXAMPLE

A flocculent is added in a suitable manner and quantity to the starting material, meta or ortho-titanic acid. For example, 1 to 2% by weight of ortho-silicic acid or derivatives thereof are added to an aqueous suspension of meta or orthotitanic acid, whereupon a pH value in the range from slightly acidic to neutral is established. This mixture is agglomerated in an ensuing hydrothermal process step. This hydrothermal process step is preferably performed in an autoclave at temperatures of 180° C. and at the corresponding autogenous vapor pressure of the water that prevails at this temperature. Depending upon the temperature selection, the duration of treatment in the autoclave can range from hours (at 180°) to days (at a correspondingly low temperature). Due to this process step, an influence is exerted upon the formation of the primary grain sizes, in other words the size of the microcrystallites that form, and the secondary grain sizes, in other words the size of the agglomerates of the microcrystallites. The primary grain size is on the order of 10 to 30 nm and the secondary grain size is on the order of 2 to 20 um. The product obtained is freed of water by means of filtration, then dried, and subsequently calcined at approximately 300° to 500° C.

If other flocculents, such as phosphorus in the form of phosphoric acid, or molybdenum compounds in the forms of ammonium molybdate, are used instead of the silicic acid mentioned above, other pH values are consequently established in the aqueous suspension, depending on the strength of the acids used. Ammonium vanadate, ammonium molybdate, ammonium tungstate, phosphoric acid, sulfuric acid, graphite powder and soluble silicic acid compounds are particularly well suited as flocculents. If silicic acid, molybdenum compounds and tungsten compounds are used as flocculents, then at the same time the proportion of the titanic acid that is present in the anatase form is increased as compared with that present in the rutile form.

I claim:

1. In a method for making a catalyst containing titanium oxide as a chief ingredient and derived from a titania source starting material selected from the group of titania acids consisting of meta-titanic acid, ortho-titanic acid and mixtures thereof, the improvement which comprises the steps of adding to dissolved starting material an acidic, water-soluble flocculent selected from the group consisting of soluble vanadates, silicic acid derivatives, sulfuric acid, soluble phosphates, phosphoric acid, soluble molybdates, soluble tungstates, and acidic particulate carbon suspensions and then treating the mixture by a hydrothermal process consisting of the steps of elevating the temperature of the mixture of starting material and flocculent while maintaining said mixture at the autogenously-generated pressure.

2. Method according to claim 1, which comprises using ammonium vanadate as the flocculent.

3. Method according to claim 1, which comprises using soluble vanadium compounds as the flocculent.

4. Method according to claim 1, which comprises using soluble phosphates as the flocculent.

5. Method according to claim 1, which comprises using phosphoric acid as the flocculent.

6. Method according to claim 1, which comprises using carbon as the flocculent.

7. Method according to claim 1, which comprises using graphite powder as the flocculent.

8. Method according to claim 1, which comprises using ammonium molybdate as the flocculent.

9. Method according to claim 1, which comprises using soluble tungsten compounds as the flocculent.

10. Method according to claim 1, which comprises using sulfuric acid as the flocculent.

11. The method according to claim 1, which comprises shifting the titanium oxide preparation in the direction of increased rutile content thereof by means of suitable additions of rutilizing promoters selected from the group consisting of lithium salts, calcium salts, and copper oxide to the mixture of titania source materials with said acidic water-soluble flocculents before said hydrothermal step.

12. The method according to claim 1, wherein, after said hydrothermal step, the liquid is separated by decanting from said product.

13. The method according to claim 1, wherein said flocculent-agglomerated product is separated from the liquid, dried and calcined.

14. The method according to claim 13, wherein said process includes a shaping step subsequent to said separation step.

15. The method according to claim 14, wherein said shaping step is performed with or without an underlying substrate.

16. The method according to claim 14, which comprises subsequently calcining the product after an interposed shaping operation selected from extrusion, coating of plates, filling of expanded metal or meshes-operations on said treated product.

17. The method according to claim 14, which comprises subsequently calcining the treated product before an interposed shaping operation selected from extrusion, coating of plates, filling of expanded metal or meshes-operations on said treated product.

* * * * *